United States Patent [19]

Scholl

[11] Patent Number: 5,260,481

[45] Date of Patent: Nov. 9, 1993

[54] PROCESS FOR THE CONDITIONING AND/OR PURIFICATION OF ORGANIC ISOCYANATES

[75] Inventor: Hans-Joachim Scholl, Cologne, Fed. Rep. of Germany

[73] Assignee: Bayer Aktiengesellschaft, Leverkusen, Fed. Rep. of Germany

[21] Appl. No.: 860,621

[22] Filed: Mar. 30, 1992

[30] Foreign Application Priority Data

Apr. 6, 1991 [DE] Fed. Rep. of Germany ....... 4111212

[51] Int. Cl.$^5$ .................. C07C 263/20; C07C 263/10
[52] U.S. Cl. .................... 560/352; 524/139; 524/262; 556/404; 556/428; 560/333
[58] Field of Search .............. 560/352, 333; 556/404, 556/428

[56] References Cited

U.S. PATENT DOCUMENTS

| | | | |
|---|---|---|---|
| 3,759,971 | 9/1973 | Cuscurida et al. | 560/352 |
| 4,246,187 | 1/1981 | Yabroff | 560/352 |
| 4,260,554 | 4/1981 | Ohlinger et al. | 560/333 |
| 4,372,891 | 2/1983 | Hilbert et al. | 560/352 |
| 4,499,023 | 2/1985 | Mitrowsky et al. | 560/352 |
| 4,661,627 | 4/1987 | Regelman | 560/352 |
| 4,774,357 | 9/1988 | Keggenhoff et al. | 560/352 |
| 5,068,402 | 11/1991 | Pedain et al. | 560/331 |

FOREIGN PATENT DOCUMENTS 1097219  1/1968  United Kingdom .

OTHER PUBLICATIONS

Patent Abstract of Japan, vol. 6, No. 165 (C-121),(1043) Aug. 28, 1992, Abstract of JP-A-57/082,358, (Mitsui Toatsu Kagaku K.K.), May 22, 1982.
Abstract of JP-9-0/140,277, (Dainippon Ink and Chemical Inc), May 29, 1990.

*Primary Examiner*—José G. Dees
*Assistant Examiner*—Vera C. Clarke
*Attorney, Agent, or Firm*—Joseph C. Gil; Thomas W. Roy

[57] ABSTRACT

The present invention relates to a process for the conditioning and/or purification of organic isocyanates by a) mixing organic isocyanates at 20° to 150° C. with 0.001 to 1 mole %, based on the isocyanate, of a silylated acid corresponding to the formula $$X\text{-}[Si(CH_3)_3]_n$$

wherein

X represents the neutral acid residue obtained by removing the acidic hydrogen atoms from an n-basic acid having a pKa value of at most 3, with the exception of hydrohalic acids and n is an integer from 1 to 3, and b) optionally working up the resulting mixture by distillation after a residence time of at least 5 minutes.

15 Claims, No Drawings

PROCESS FOR THE CONDITIONING AND/OR PURIFICATION OF ORGANIC ISOCYANATES

BACKGROUND OF THE INVENTION

1. Field of the Invention

This invention relates to a new process for the conditioning and/or purification of organic isocyanates in which the isocyanates are mixed with certain silylated acids and the mixtures obtained are optionally worked up by distillation.

2. Description of the Prior Art

Production-related impurities of varying types and quantities in isocyanates are the cause of reactivity fluctuations and color problems, and affect the ultimate products produced from these isocyanates. A limitation, i.e., narrowing of the specification range, particularly in the case of industrial isocyanates, is a meaningful objective for their improved and, thus, more economical handling.

Accordingly, an object of the present invention is to provide a new process for the conditioning and/or purification of organic isocyanates to reduce their level of impurities and assist in overcoming the deficiencies discussed above.

This object may be achieved by the process according to the invention which is described in more detail hereinafter. In accordance with the process according to the invention a small quantity of certain silylated acids, which are described in more detail hereinafter, is added to the isocyanates to be treated and optionally the resulting mixtures are worked up by distillation.

SUMMARY OF THE INVENTION

The present invention relates to a process for the conditioning and/or purification of organic isocyanates by a) mixing organic isocyanates at 20° to 150° C. with 0.001 to 1 mole %, based on the isocyanate, of a silylated acid corresponding to the formula

$$X\text{-}[Si(CH_3)_3]_n$$

wherein
X represents the neutral acid residue obtained by removing the acidic hydrogen atoms from an n-basic acid having a pKa value of at most 3, with the exception of hydrohalic acids and
n is an integer from 1 to 3, and b) optionally working up the resulting mixture by distillation after a residence time of at least 5 minutes.

DETAILED DESCRIPTION OF THE INVENTION

Any organic isocyanates may be used as starting materials for the process according to the invention. However, the process according to the invention is preferably used for the conditioning and/or purification of organic diisocyanates of the type used in polyurethane chemistry.

Organic diisocyanates such as these include, in particular (cyclo)aliphatic diisocyanates such as 1,6-diisocyanatohexane (HDI), 1-isocyanato-3,3,5-trimethyl-5-isocyanatomethyl cyclohexane (IPDI), 4,4'-diisocyanatodicyclohexyl methane (HMDI) and mixtures of these aliphatic diisocyanates. Aromatic diisocyanates, such as 2,4- and/or 2,6-diisocyanatotoluene (TDI), 2,2'-, 2,4'- and/or 4,4'-diisocyanatodiphenyl methane (MDI) and mixtures of these aromatic diisocyanates, may also be used as starting materials in accordance with the invention.

Modified polyisocyanates may also be used as starting materials according to the invention. Of particular interest are the modified polyisocyanates obtained by the partial trimerization of the isocyanate groups of HDI, IPDI and mixtures of HDI and IPDI to produce the corresponding isocyanurate-modified polyisocyanates which contain the starting diisocyanates mentioned and the isocyanurate-modified polyisocyanates formed. When these mixtures are used as starting polyisocyanates for the process according to the invention, the additive crucial to the invention is preferably added when the trimerization reaction is to be terminated because, in many cases, the additives crucial to the invention also perform the function of catalyst poison and, thus, acts as a stopper for the trimerization reaction. Particularly high-quality trimerization products of the (cyclo)aliphatic diisocyanates mentioned are obtained when diisocyanates pretreated in accordance with the invention are used as starting diisocyanates and the trimerization products are subsequently treated as previously described.

The additives crucial to the invention are silylated acids corresponding to the formula

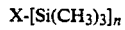

$$X\text{-}[Si(CH_3)_3]_n$$

wherein X and n are as defined above. X is preferably the neutral acid residue of an oxygen-containing acid containing n acidic hydrogen atoms and having a maximum pKa value of 2.

Suitable silylated acids include the corresponding silylated sulfonic acids such as trifluoromethane sulfonic acid trimethyl silyl ester and methane sulfonic acid trimethyl silyl ester; and silylated esters of acids of phosphorus such as phosphoric acid trim-(trimethyl silyl ester) or phosphoric acid diethyl ester trimethyl silyl ester.

The silylated acids are added to the starting isocyanates in an amount of 0.001 to 1.0 mole %, preferably in 0.001 to 0.1 mole %, based on the isocyanate. The optimal quantity may readily be determined in a preliminary test. The addition is made at a temperature of 20° to 150° C., preferably 50° to 120° C.

The mixture obtained is preferably worked up by distillation after a holding time of at least 5 minutes, preferably at least 30 minutes. When distillable starting isocyanates are used, this is understood to mean their purification by distillation, for example in a thin-layer evaporator; whereas, when mixtures of monomeric diisocyanates and non-distillable isocyanurate-modified polyisocyanates are used, working up by distillation is understood to mean removing the volatile starting diisocyanates by distillation. This distillation-based method of working up is also preferably carried out using thin-layer evaporators. The distillation conditions are selected so that the distillation residues which represent the product contain at most 2.0% by weight, preferably at most 0.5% by weight, of monomeric starting diisocyanates.

The isocyanates which have been treated in accordance with the invention show comparatively reduced reactivity fluctuations and contain reduced traces of coloring impurities. This can be demonstrated particularly easily on the basis of secondary reactions such as the production of isocyanurate-modified polyisocyanates by partial trimerization of the isocyanate groups of monomeric diisocyanates which have been treated in accordance with the invention.

The conditioning according to the invention is interesting in two respects in connection with the production of isocyanurate-modified, lacquer-quality polyisocyanates from (cyclo)aliphatic starting diisocyanates. On the one hand it is advantageous for the reasons just mentioned to use diisocyanates pretreated in accordance with the invention as starting material for the production of these lacquer-quality polyisocyanates. On the other hand the addition of the additive according to the invention to the reaction mixture formed during the trimerization reaction before it is worked up by distillation not only results in conditioning, but also, in particular, in an improvement in the color values not only of the excess starting diisocyanates recovered by distillation, which are used for a further reaction, but also of the products, i.e., the distillation residues obtained during working-up by distillation.

This applies in particular to the known trimerization of (cyclo)aliphatic diisocyanates, more particularly HDI, using quaternary ammonium hydroxides or, more preferably, quaternary ammonium fluorides, as the trimerization catalyst. When these catalysts are used, the silylated acids also act as a catalyst poison so that the conditioning according to the invention results in termination of the trimerization reaction at the particular degree of trimerization required.

The invention is further illustrated but is not intended to be limited by the following examples in which all parts and percentages are by weight unless otherwise specified.

EXAMPLES

Starting materials

Quaternary ammonium salt I (according to DE 38 27 596)

20 g of a commercially available quaternary ammonium chloride consisting essentially of N-methyl-N,N,N-trialkyl ammonium chloride containing $C_{8-10}$ alkyl groups (Aliquat 336, a product of Fluka GmbH, D 7910 Neu-Ulm), dissolved in 60 g of ethanol, were added with stirring at room temperature to 2.9 g of potassium fluoride in 50 g of ethanol. After 60 minutes, insoluble constituents were filtered off, 476 g of 2-ethyl-1-hexanol were added to the filtrate and ethanol was removed under vacuum. A solution of a quaternary ammonium fluoride in ethyl-1-hexanol having a fluoride content of 0.07 mmol/g was obtained.

Quaternary ammonium salt II (according to DE 38 06 276)

0.5% by weight N,N,N-trimethyl-N-benzyl ammonium hydroxide in 2-ethylhexane-1,3-diol.

EXAMPLE 1

Reaction of HDI with trifluoromethane sulfonic acid trimethyl silyl ester (TMS triflate)

3,528 g (21 moles) of technical HDI were stirred for 1 hour at 100° C. with 7.3 g of a 2.3% TMS triflate solution in HDI. The HDI was subsequently recovered by thin-layer distillation.

EXAMPLE 2

Reaction of HDI with phosphoric acid tris-(trimethyl silyl ester)

3,360 g (20 moles) of technical HDI were stirred for 1 hour at 100° C. with 7 g of a 1% phosphoric acid tris-(trimethyl silyl ester) solution in HDI. The HDI was subsequently recovered by thin-layer distillation.

EXAMPLE 3

Partial trimerization of the pretreated diisocyanates of Examples 1 and 2 in comparison with untreated HDI produced in the same way to document the advantages afforded by the invention, i.e., an improvement in activity and in color quality 840 g quantities (5 moles) of HDI were subjected to partial trimerization for 7 hours at 55° C. using ammonium salt I as catalyst. After termination of the reaction with the particular catalyst poison, the products were freed from unreacted HDI by thin-layer distillation. The results are set forth in Table 1 below.

TABLE 1

|  | Example 3a | Example 3b | Comparison Example 3c |
|---|---|---|---|
| Starting product | HDI (Example 1) | HDI (Example 2) | HDI (untreated) |
| Catalyst | 5 g | 4 g | 5 g |
| Beginning: $n_D^{23}$ | 1.4520 | 1.4520 | 1.4520 |
| End: $n_D^{23}$ | 1.4622 | 1.4650 | 1.4598 |
| Catalyst poison[1] | TMS triflate | Phosphoric acid tris-(trimethyl silyl ester) | Phosphoric acid dibutyl ester |
| End Products: |  |  |  |
| Yield | 22.5% | 27.5% | 17.7% |
| NCO | 23.1% | 22.8% | 22.9% |
| Color quality | Good: colorless | Good: colorless | Poor: Yellow |

The clear superiority of the process products according to the invention is reflected in the higher conversion (improvement in reactivity) and in the improved color quality.
[1] Quantity: 30 mole %, based on catalyst used

EXAMPLE 4

Partial trimerization of the pretreated diisocyanate of Example 2 in comparison with untreated HDI produced in the same way using quaternary ammonium salt II as the trimerization catalyst to document the advantages afforded by the invention, i.e., an improvement in activity and in color quality 840 g quantities (5 moles) of HDI were subjected to partial trimerization for 7 hours at 55° C. using ammonium salt II as catalyst. After termination with the particular catalyst poison, the products were freed from unreacted HDI by thin-layer distillation. The results are shown in Table 2 below.

TABLE 2

|  | Example 4a | Comparison Example 4b |
|---|---|---|
| Starting product | HDI (Example 2) | HDI (untreated) |
| Catalyst | 8 g | 9 g |
| Beginning: $n_D^{23}$ | 1.4520 | 1.4520 |
| End: $n_D^{23}$ | 1.4643 | 1.4566 |
| Catalyst poison[1] | Phosphoric acid tris-(trimethyl silyl ester) | Phosphoric acid dibutyl ester |
| End products: |  |  |
| Yield | 26.9% | 11.6% |
| NCO | 22.1% | 21.0% |

TABLE 2-continued

|  | Example 4a | Comparison Example 4b |
|---|---|---|
| Color quality | Good: colorless | Poor: yellow |

The superiority of the products according to the invention was reflected in the higher conversion (improvement in reactivity) and in the improved color quality.

1) Quantity: 40 mole %, based on catalyst used

EXAMPLE 5

Reaction of HDI/IPDI (4:1 molar ratio) with trifluoromethane sulfonic acid trimethyl silyl ester (TMS triflate)

A mixture of 672 g (4 moles) of technical HDI and 222 g of (1 mole) technical IPDI was heated for 0.5 h to 100° C. with 3.4 g of a 2.3% TMS triflate solution in HDI and recovered by thin-layer distillation.

EXAMPLE 6

Partial trimerization of the pretreated HDI/IPDI mixture of Example 5 in comparison with an untreated HDI/IPDI mixture (4:1 molar ratio) produced in the same way 447 g quantities (2 moles HDI, 0.5 moles IPDI) of the HDI/IPDI mixture were subjected to partial trimerization for 7 hours at 55° C. using ammonium salt I as catalyst. After termination with the particular catalyst poison, the products were freed from unreacted HDI-/IPDI by thin-layer distillation. The results are set forth in Table 3 below.

TABLE 3

|  | Example 6a | Comparison Example 6b |
|---|---|---|
| Starting product | HDI/IPDI mixture of Example 5 | HDI/IPDI (untreated) |
| Catalyst | 5.5 g | 5.5 g |
| Beginning: $n_D^{23}$ | 1.4595 | 1.4595 |
| End: $n_D^{23}$ | 1.4679 | 1.4643 |
| Catalyst poison[1)] | TMS triflate | Phosphoric acid dibutyl ester |
| End products: |  |  |
| Yield | 16.8% | 9.5% |
| NCO | 21.7% | 21.6% |
| Color quality | Good: light yellow | Poor: yellow |

The clear superiority of the products according to the invention was reflected in the higher conversion (improvement in reactivity) and in the improved color quality.

1) Quantity: 20 mole %, based on catalyst used Comparison Examples—to illustrate the improved activity of the silyl compounds crucial to the invention as stoppers in comparison with phosphoric acid dibutyl ester

A) Partial trimerization of HDI 3,528 g (21 moles) of technical HDI were heated with stirring under nitrogen to 55° C., followed by the addition of 14 g of quaternary ammonium salt I. After 4 hours, the refractive index $n_D^{23}$ had increased from 1.4520 to 1.4606.

B) Stopping of the crude solution

Three 672 g samples were taken and to each was immediately added 0.5 mmol of catalyst poison to terminate the reaction. The catalyst poisons according to the invention effectively stabilized the crude solution over the test period while the isocyanate content of the comparison sample decreased over the test period. The test was carried out by measurement of the refractive index; the test period was 84 days. The results are set forth in Table 4 below.

TABLE 4

|  | Sample a | Sample b | Sample c |
|---|---|---|---|
| Quantity | 672 g | 672 g | 672 g |
| Catalyst poison | Trifluoromethane sulfonic acid trimethyl silyl ester | Phosphoric acid tris-(trimethyl silyl ester) | Phosphoric acid di butyl ester |
| $n_D^{23}$: after stopping | 1.4609 | 1.4608 | 1.4609 |
| $n_D^{23}$: after 84 days | 1.4610 | 1.4608 | 1.4688 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the conditioning and/or purification of an organic isocyanate which comprises
    a) mixing said organic isocyanate at 20° to 150° C. with 0.001 to 1 mole %, based on the isocyanate, of a silylated acid corresponding to the formula $$X\text{-}[Si(CH_3)_3]_n$$

wherein
    X represents the neutral acid residue obtained by removing the acidic hydrogen atoms from an n-basic acid having a pKa value of at most 3, with the exception of hydrohalic acids and
    n is an integer of 1 to 3, and
    b) optionally working up the resulting mixture by distillation after a residence time of at least 5 minutes.

2. The process of claim 1 wherein said organic isocyanate comprises a member selected from the group consisting of 1,6-diisocyanatohexane, 1-isocyanato-3,3,5-trimethyl-5-isocyanatomethyl cyclohexane, 4,4'-diisocyanatodicyclohexyl methane and mixtures of these diisocyanates.

3. The process of claim 1 wherein said organic isocyanate comprises (i) 2,4- and/or 2,6-diisocyanatotoluene, (ii) 2,2'-, 2,4'- and/or 4,4'-diisocyanatodiphenyl methane or (iii) mixtures of these diisocyanates.

4. The process of claim 1 wherein
    said organic isocyanate is a mixture of (i) 1,6-diisocyanatohexane and/or 1-isocyanato-3,3,5-trimethyl-5-isocyanatomethyl cyclohexane and (ii) an isocyanurate-modified polyisocyanate prepared from (i) by catalytic trimerization and
    said mixture is subsequently subjected to working up by distillation to remove (i) and obtain a substantially monomer-free, isocyanurate-modified polyisocyanate.

5. The process of claim 1 wherein X represents the neutral acid residue of an oxygen-containing acid having a pKa value of at most 2.

6. The process of claim 2 wherein X represents the neutral acid residue of an oxygen-containing acid having a pKa value of at most 2.

7. The process of claim 3 wherein X represents the neutral acid residue of an oxygen-containing acid having a pKa value of at most 2.

8. The process of claim 4 wherein X represents the neutral acid residue of an oxygen-containing acid having a pKa value of at most 2.

9. The process of claim 1 wherein the silylated acid comprises trifluoromethane sulfonic acid trimethyl silyl ester or phosphoric acid tris-(trimethyl silyl ester).

10. The process of claim 2 wherein the silylated acid comprises trifluoromethane sulfonic acid trimethyl silyl ester or phosphoric acid tris-(trimethyl silyl ester).

11. The process of claim 3 wherein the silylated acid comprises trifluoromethane sulfonic acid trimethyl silyl ester or phosphoric acid tris-(trimethyl silyl ester).

12. The process of claim 4 wherein the silylated acid comprises trifluoromethane sulfonic acid trimethyl silyl ester or phosphoric acid tris-(trimethyl silyl ester).

13. A process for the conditioning and/or purification of an organic isocyanate which comprises
    a) mixing an organic isocyanate comprising 1,6-diisocyanatohexane and/or 1-isocyanato-3,3,5-trimethyl-5-isocyanatomethyl cyclohexane at 20° to 150° C. with 0.001 to 1 mole %, based on the isocyanate, of a silylated acid corresponding to the formula $$X-[Si(CH_3)_3]_n$$

wherein
    X represents the neutral acid residue obtained by removing the acidic hydrogen atoms from an n-basic acid having a pKa value of at most 3, with the exception of hydrohalic acids and
    n is an integer of 1 to 3,
    b) working up the resulting mixture by distillation after a residence time of at least 5 minutes,
    c) preparing a blend of (i) 1,6-diisocyanatohexane and/or 1-isocyanato-3,3,5-trimethyl-5-isocyanatomethyl cyclohexane and (ii) an isocyanurate-modified polyisocyanate by the catalytic trimerization of the product obtained in b)
    d) mixing said blend at 20° to 150° C. with 0.001 to 1 mole %, based on the isocyanate, of said silylated acid and
    e) working up the mixture formed in d) by distillation after a residence time of at least 5 minutes with recovery of a substantially monomer-free, isocyanurate-modified polyisocyanate.

14. The process of claim 13 wherein X represents the neutral acid residue of an oxygen-containing acid having a pKa value of at most 2.

15. The process of claim 13 wherein the silylated acid comprises trifluoromethane sulfonic acid trimethyl silyl ester or phosphoric acid tris-(trimethyl silyl ester).

* * * * *